United States Patent
Koehler et al.

(10) Patent No.: US 10,417,761 B2
(45) Date of Patent: Sep. 17, 2019

(54) BEAM HARDENING CORRECTION FOR SCANNING DARK FIELD AND PHASE CONTRAST IMAGING

(71) Applicant: KONINKLIJKE PHILIPS N.V., Eindhoven (NL)

(72) Inventors: Thomas Koehler, Norderstedt (DE); Heiner Daerr, Hamburg (DE); Ewald Roessl, Ellerau (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 17 days.

(21) Appl. No.: 15/571,893

(22) PCT Filed: May 6, 2016

(86) PCT No.: PCT/EP2016/060238
§ 371 (c)(1),
(2) Date: Nov. 6, 2017

(87) PCT Pub. No.: WO2016/177903
PCT Pub. Date: Nov. 10, 2016

(65) Prior Publication Data
US 2018/0137618 A1    May 17, 2018

(30) Foreign Application Priority Data
May 7, 2015  (EP) .................................... 15166774

(51) Int. Cl.
*G06K 9/00*   (2006.01)
*A61B 6/00*   (2006.01)
(Continued)

(52) U.S. Cl.
CPC ............ *G06T 7/0012* (2013.01); *A61B 6/502* (2013.01); *G06T 11/005* (2013.01); *G06T 2207/10081* (2013.01); *G06T 2207/30068* (2013.01)

(58) Field of Classification Search
USPC ........ 382/100, 103, 106–107, 128–134, 154, 382/162, 168, 173, 181, 199, 232, 254,
(Continued)

(56) References Cited

U.S. PATENT DOCUMENTS

| 7,532,704 B2 * | 5/2009 | Hempel | ................. A61B 6/032 378/145 |
| 2011/0243305 A1 * | 10/2011 | Tada | .................... A61B 6/4291 378/87 |

(Continued)

FOREIGN PATENT DOCUMENTS

| WO | 2012029039 A1 | 3/2012 | |
| WO | WO 2012/029039 | * 3/2012 | ............... A61B 6/03 |

(Continued)

OTHER PUBLICATIONS

Kottler, C. et al "Grating Interferometer Based Scanning Setup for Hard X-Ray Phase Contrast Imaging", Review of Scientific Instruments, vol. 78, 043710, 2007.
(Continued)

*Primary Examiner* — Seyed H Azarian
(74) *Attorney, Agent, or Firm* — Larry Liberchuk

(57) ABSTRACT

An apparatus and related method for processing image data supplied by a scanning phase contrast or dark-field imaging apparatus (MA). Beam hardening artifact in phase contrast and dark-field imaging can be reduced by applying a beam hardening processing operation by a beam hardening processing module (BHC) in respect of a plurality of detector readings that contribute signals to the same image pixel
(Continued)

position or geometric ray of an imaging region of the apparatus (MA). In one embodiment, a phantom body (PB) is used to acquire calibration data on which the beam hardening processing is based.

12 Claims, 9 Drawing Sheets

(51) Int. Cl.
  *G06T 7/00* (2017.01)
  *G06T 11/00* (2006.01)
(58) Field of Classification Search
  USPC ..... 382/260, 274–276, 286–291, 312; 378/4, 378/21, 36, 19, 87, 145
  See application file for complete search history.

(56) References Cited

U.S. PATENT DOCUMENTS

2015/0124927 A1* 5/2015 Koehler ............... G06T 11/006 378/19
2016/0095562 A1* 4/2016 Baturin ................ A61B 6/484 378/36

FOREIGN PATENT DOCUMENTS

WO 2015014677 A1 2/2015
WO 2015090949 A1 6/2015

OTHER PUBLICATIONS

Momose, A. et al "High-Speed X-Ray Phase Imaging and X-Ray Phase Tomography with Talbot Intererometer and White Synchrotron Radiation", Optics Express, vol. 17, No. 15, pp. 12540, 2009.
Donath, T. et al "Inverse Geometry for Grating-Based X-Ray Phase-Contrast Imaging", Journal Applied Physics, vol. 106, pp. 054703, 2009.
Weitkamp, Timm et al "X-Ray Phase Imaging with a Grating Interferometer", Optics Express, vol. 13, No. 16, pp. 6296-6304, 2005.
Bevins, Nicholas et al "Beam Hardening in X-Ray Differential Phase Contrast Computed Tomography", Medical Imaging 2011: Physics of Medical Imaging, vol. 7921, No. 1, Mar. 2011, pp. 1-6.
Chabior, Michael et al "Beam Hardening Effects in Grating-based X-Ray Phase-Contrast Imaging", Medical Physics, vol. 38, No. 3, Feb. 2011, pp. 1189-1195.
Epple, Franz M. et al "Phase Unwrapping in Spectal X-Ray Differential Phase-Contrast Imaging with an Energy-Resolving Photon-Counting Pixel Detector", IEEE Transactions on Medical Imaging, vol. 34, No. 3, Mar. 2015.
Jerjen, Iwan et al "Reduction of Phase Artifacts in Differential Phase Contrast Computer Tomography", Optics Express, vol. 19, No. 14, Jun. 2011, pp. 13604-13611.

* cited by examiner

BEAM HARDENING CORRECTION FOR SCANNING DARK FIELD AND PHASE CONTRAST IMAGING

CROSS-REFERENCE TO PRIOR APPLICATIONS

This application is the U.S. National Phase application under 35 U.S.C. § 371 of International Application No. PCT/EP2016/060238, filed on May 6, 2016, which claims the benefit of European Patent Application No. 15166774.8, filed on May 7, 2015. These applications are hereby incorporated by reference herein.

FIELD OF THE INVENTION

The invention relates to an image signal processing system, to a method for processing data supplied by a differential phase contrast and/or dark field imager of the scanning type, to a method of producing calibration data, to a scanning differential phase contrast or dark-field imaging apparatus, to a computer program element, and to a computer readable medium.

BACKGROUND OF THE INVENTION

In some scanning imaging systems such as scanning mammography systems, the object to be imaged is scanned by movement of the imaging system's detector. Some of these scanning imaging systems include an interferometer arrangement that allows grating based phase contrast or dark-field imaging. See for instance C. Kottler et al, "Grating interferometer based scanning setup for hard x-ray phase contrast imaging", Rev. Sci. Instrum. 78, 043710 (2007).

The proposition in phase contrast imaging is that radiation intensity as detected at the detector does not only encode information on attenuation (traditional x-ray radiography is based on this) but also holds information on refraction as well as small angle scattering (related to the so-called dark-field image) experienced by the radiation in its passage through the object to be imaged.

Scanning based phase contrast or dark-field imaging is complicated by the fact, that due to the scanning motion, image information redundancy is introduced. The image information on phase contrast or dark-field contrast is "spread out" across a plurality of pixels. Also, it has been observed that phase contrast and dark-field imagery occasionally suffer from artifacts.

SUMMARY OF THE INVENTION

There may therefore be a need for a method and related system to help reduce beam hardening effect artifacts in scanning based phase contrast or dark-field imaging.

The object of the present invention is solved by the subject matter of the independent claims where further embodiments are incorporated in the dependent claims. It should be noted that the following described aspect of the invention equally applies to the method for processing data supplied by a differential phase contrast and/or dark field imager of the scanning type, to the imaging apparatus, to the computer program element and to the computer readable medium.

According to a first aspect of the invention, there is provided an image signal processing system for processing data supplied by a differential phase contrast and/or dark field imager of the scanning type having an x-ray source for emitting radiation, a detector for detecting radiation, and an interferometer arranged at least partly between said x-ray source and said detector, the system comprising:

an input port for receiving data in form of intensity values $m_i$ that correspond to one and the same geometrical ray, the intensity values $m_i$ acquired i) using different detector pixels of the detector in a scan operation by the imager of an object or ii) using a, respective, single detector pixel whilst at least a part of the interferometer is moved past said single detector pixel in a scan operation;

a beam hardening processing component configured to apply, for a given image pixel position as per said geometrical ray, a beam hardening processing operation in respect of said intensity values $m_i$, thereby obtaining at least one interferometric reference parameters including at least one of a reference intensity and a reference visibility for said image pixel position;

reconstructor configured to reconstruct from said intensity values and said at least one interferometric reference parameters at least one of a phase signal and a dark-field signal; and an output port for outputting at least one of said phase signal and said dark-field signal.

According to one embodiment the beam hardening processing operation includes computing, for said intensity values, said at least one interferometric reference parameter as a function of an indicator parameter that relates i) to a mean attenuation experienced by the radiation along said geometrical ray and/or ii) to a property of the object to be imaged.

According to one embodiment the indicator parameter comprises i) an estimate of a mean attenuation previously reconstructed from the received intensities $m_i$ or ii) a surrogate for said mean attenuation.

According to one embodiment a functional relationship between the indicator parameter and the at least one interferometric parameter is different for different ones of the detector pixels or the respective single detector pixels.

According to one embodiment the respective functional relationships are encoded i) as one more look-up-tables compiled from calibration data or ii) as one or more functional expressions.

According to one embodiment the calibration data is derived from calibration detector readings acquired by the imager in i) a blank scan and at least one phantom scan for a given phantom thickness or ii) a plurality of phantom scans for different phantom thicknesses.

According to one embodiment the phantom is configured so as to have an adjustable thickness to achieve the different thicknesses.

According to one embodiment the at least one reference interferometric parameter include, per detector pixel or for said respective single detector pixel, at least one of a visibility and an input intensity.

According to a second aspect there is provided a scanning differential phase contrast, DCPI, or dark-field imaging apparatus that includes an image processing system as per any one of the above.

In sum, there is proposed a system to efficiently compute one or more reference parameters for dark-field or phase contrast imaging where imaging information is spread "spatially" across different detector pixels (e.g. when scanning the detector) or is spread "temporally" across different measurement instances for a given (single) detector pixel (e.g., when the scanning motion is achieved by moving at least a part (e.g., a grating structure) of the interferometer whilst the detector is stationary. The so obtained reference parameter allow for a reconstruction of phase contrast and/or dark-field imagery where beam hardening artifacts are reduced or even eliminated.

According to a third aspect there is provided a method for processing data supplied by a differential phase contrast imager or a dark-field imager of the scanning type having an x-ray source for emitting radiation, a detector for detecting radiation, and an interferometer arranged at least partly between said x-ray source (XR) and said detector, the method comprising:

receiving data in form of intensity values $m_i$ that correspond to one and the same geometrical ray, the intensity values $m_i$ acquired i) using different detector pixels of the detector in a scan operation by the imager of an object or ii) using a, respective, single detector pixel whilst at least a part of the interferometer is moved past said single detector pixel in a scan operation;

applying, for a given image pixel position as per said geometrical ray, a beam hardening processing operation in respect of said intensity values $m_i$, thereby obtaining at least one interferometric reference parameters including at least one of a reference intensity and a reference visibility for said image pixel position;

reconstructing from said intensity values and said at least one interferometric reference parameters at least one of a phase signal and a dark-field signal; and outputting at least one of said phase signal and said dark-field signal.

According to a fourth aspect there is provided a method of producing calibration data for beam hardening effect processing in scanning phase contrast or dark-field imaging, comprising:

acquiring, with a scanning detector or x-ray source of a differential phase contrast imager, calibration detector readings in i) a blank scan and at least one phantom scan for a given phantom thickness or ii) a plurality of phantom scans for different phantom thicknesses;

reconstructing, per detector pixel and per phantom thickness or blank scan, interferometric reference parameters from the calibration detector readings.

According to one embodiment, the method comprises reconstructing, per image pixel and per phantom thickness or blank scan, respective indictor parameter indicative of different mean attenuation levels as per the different phantom thickness or blank scan.

According to one embodiment, the method comprises storing the interferometric reference parameters in association with respective ones of the indictor parameters according to phantom thickness or blank scan.

The present invention allows for useful application in a clinical environment such as a hospital. More specifically, the present invention is very suitable for application in imaging modalities such as mammography, diagnostic radiology, interventional radiology and computed tomography (CT) for the medical examination of patients. In addition, the presentation invention allows for useful application in an industrial environment. More specifically, the present invention is very suitable for application in non-destructive testing (e.g. analysis as to composition, structure and/or qualities of biological as well non-biological samples) as well as security scanning (e.g. scanning of luggage on airports).

BRIEF DESCRIPTION OF THE DRAWINGS

Exemplary embodiments of the invention will now be described with reference to the following drawings wherein.

DETAILED DESCRIPTION OF EMBODIMENTS

Figure 1:
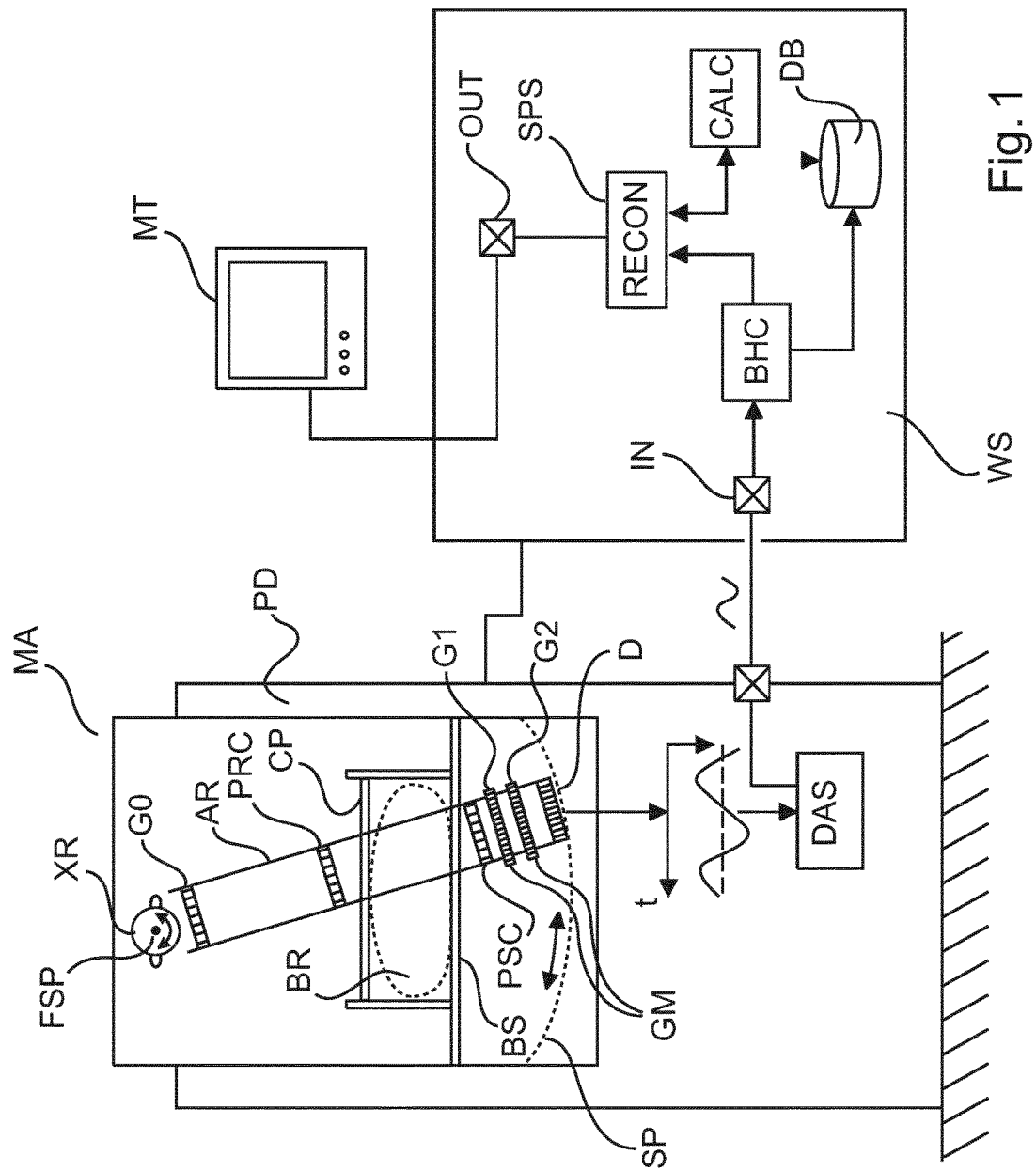
FIG. 1 shows an imaging arrangement.

With reference to FIG. 1 there is shown a phase contrast or dark-field imaging radiography apparatus MA. In one embodiment the phase contrast imaging apparatus is a mammography apparatus of the scanner type but it will be appreciated that the following finds equal application to other scanning radiography imagers for phase contrast or dark-field imaging for instance, computed tomography CT scanners. Mammography is merely one non-limiting field of application of what is prosed herein. It will be appreciated that the term "arm" as used herein corresponds to the rotatable gantry in CT scanner systems.

The imaging system MA is connected via suitable interface means and across a communication network to a workstation WS. In general, workstation WS is a computing system with which a clinician ("user") is able to control operation of the imaging system. According to one embodiment, there is also a display unit or monitor M which is controlled by work station WS and which allows displaying of images that are acquired by the imaging system. Workstation WS runs an operating system which in turn controls execution of an image signal processing system SPS whose operation will be explained in more detail below.

The mammography apparatus MA includes a pedestal PD on which there is mounted an x-ray source XR. The x-ray source is rotatable around its focal spot FSP. The pedestal PD supports a rotatable gantry with a rotatable hollow arm RA. The arm RS is rotatable around the focal spot FS. The mammography apparatus MA includes an interferometer INF. The interferometer includes in one embodiment three gratings but other embodiments with only 2 gratings are also envisaged. In one embodiment, it is the arm/gantry includes two or more interferometric gratings (a source grating G0, and a π-phase grating G1 and/or an analyzer grating G2) that together afford the phase contrast and or dark-field imaging capability as will be explained in more detail below. G1 may also be a π/2-phase grating or other suitable phase grating. It is even possible, though not preferred, to use an absorber grating for G1 instead of a phase grating which is the preferred embodiment in medical applications but the absorber version for G1 may be called for in non-medical contexts.

At the lower end of the arm AR there is mounted a detector plate D with a radiation sensitive surface for detecting radiation emitted by source XR. The lower part of the arm also includes a gratings mounting GM itself mounted on top of the detector plate. The mounting holds one or two (preferably two) gratings G1,G2, with G1 on top of G2, and both above the detector plate, in particular, both gratings mounted above the radiation sensitive surface of the detector plate D. Source grating G0 is arranged at the upper end of the arm at an exit window of x-ray source XR. Also included in one embodiment and carried by the arm is a multi-collimator arrangement preferably a pre-collimator PRC and a post collimator PSC. The post-collimator acts to remove or at least reduce scattering but this component may be left out in certain embodiment, as the G2 grating likewise acts to remove/reduce scattering. Referring back to the interferometer arrangement INF, there are embodiments envisaged which include only two gratings (for instance G0 and G1) and no explicit G2 grating where the analyzer functionality (of grating G2) is integrated into and/or is taken up by other structures of the imager MA. For instance, in one embodiment the analyzer functionality is integrated into detector D.

There is an examination region (or imaging region) defined as recess in a housing of the mammography apparatus MA for positioning into a sample object to be imaged, for instance the patient's breast BR. Part of the mammography apparatus MA housing defines a detector housing whose upper surface serves as a breast support BS on which patient's breast BR is placed during an imaging session, the breast support thereby delimiting from below the examination region. There is also a compression plate CP or paddle which can shuttle up and down to compress the breast when placed on the breast support.

Optionally, in addition to the arm being rotatable as described above, it is also the whole gantry that is rotatable around a pivot point positioned roughly at the height of the breast support. The whole gantry can thereby be tilted to change approach angle to so afford selectively imaging at different views, for instance at CC (cranio-caudal) view (at 12 o'clock position) or MLO (mediolateral oblique) view at about 2 o'clock position.

Radiation emitted by the source XR enters the arm through an exit window and then passes through the arm towards the detector. In its passage the radiation wave interacts with the first grating G0, also referred to as the source grating G0, to establish coherence.

Briefly, the radiation flow is as follows: the radiation wave is collimated by the one or two collimators, then interacts with the breast BR if present in the examination region, thereafter interacts with the two gratings G1, G2 and is then incident on detector D. There may be also embodiments, where the breast BR is located between gratings G1 and G2.

The mammography apparatus MA is operable in two basic modes: in a blank scan mode or in an object scan mode. When in object scan mode, which is the usual mode of operation, the patients breast BR or other sample is placed in the examination region. In blank scan mode, no object or breast is present in the examination region. In object scan, detector readouts are acquired, which can be fed into a reconstructor RECON of the image signal processing system SPS to compute the phase contrast projection image and/or a small scattering ("dark field") contrast image (and, if desired, a (traditional) attenuation contrast image) in an interferometric reconstruction operation (simply referred to as reconstruction herein), sometimes also referred to as "phase retrieval" operation although this may be misleading as, for present purposes, along with the phase information, it is also the dark-field signal and the attenuation signal that is retrieved in the reconstruction. Processing and operation of module SPS will be described in more detail below.

During an object or blank scan, the lower part of the arm (and with it the detector plate and the gratings mounting GM) is motorized to move in the detector housing under breast support BS. In either mode, object or blank scan, the arm is moved in synchrony with the x-ray source rotation around its focal spot FSP so that the detector D together with the gratings G1 and G2 traces out a scanner path SP under the breast BR, if present. In other scan operation embodiments, the source XR does not rotate but only the collimator does so. In an alternative embodiment (e.g. in CT context), the entire source-detector system rotates around the patient. There are also scan operations envisaged, where the detector D remains stationary whilst it is at least a part of the interferometer INF that is movable and is scanned past the object BR. For instance, grating G1 and/or grating G2 may be moved during the scan. In general the scan path is an arc as shown in FIG. 1 but straight scan paths are also envisaged in other embodiments.

In one embodiment the mammography apparatus MA is a single or multi slit or slot system. In other words the detector D's radiation sensitive surface is formed from a single or, in general, a plurality (for example 8) of discretely arranged semi-conductor detector lines deposited on a wafer substrate obtained by a photolithographic process or other suitable detector manufacturing technique. In the central, frontal elevation of FIG. 1, those detector lines r stripes extend into the paper plane arranged side by side. Each detector line is made up of a linear sequence of detector pixels. Because of the pre- and post-collimator arrangement, the x-ray beam is essentially split up into a plurality of mini fan beams, with each fan beam irradiating at any one time exactly one of the respective detector lines, namely the one that happens to pass through said fan beam during the detector's motion. Said differently, the detector lines are being exposed to their respective mini fan beam, with each respective mini-fan beam changing direction during the scan. Whilst travelling along the scan path, each detector line will produce the respective readout at different positions on the path. In other words, unlike for systems with a 2D full field of view (fov) detector (2D detector in short), where the whole field of view acquired in a single snapshot, in the present multi-slit system according to one embodiment, after completing the scanning motion, the successive readouts of the detectors during the scan can be used to compose a single 2D image for the field of view. In systems with a 2D full fov detector, the detector pixels are arranged in rows and columns on a detector plane and not as discrete detector lines as in the multi-slit detector geometry. Useful as the multi-slit detector type may be, this is not to say that 2D detector arrangements are excluded herein. They are not. In other words, in alternative embodiments to the multi-slit detector type with discrete detector lines described above, a scanning geometry with a part or full fov 2D detector is also envisaged herein. Preferably (but necessarily), in this embodiment with the 2D detector, the scanning operation is achieved by moving one or more gratings (e.g., G0 and/or G1 and/or G2) over the field of view of the stationary 2D detector.

Figure 2:
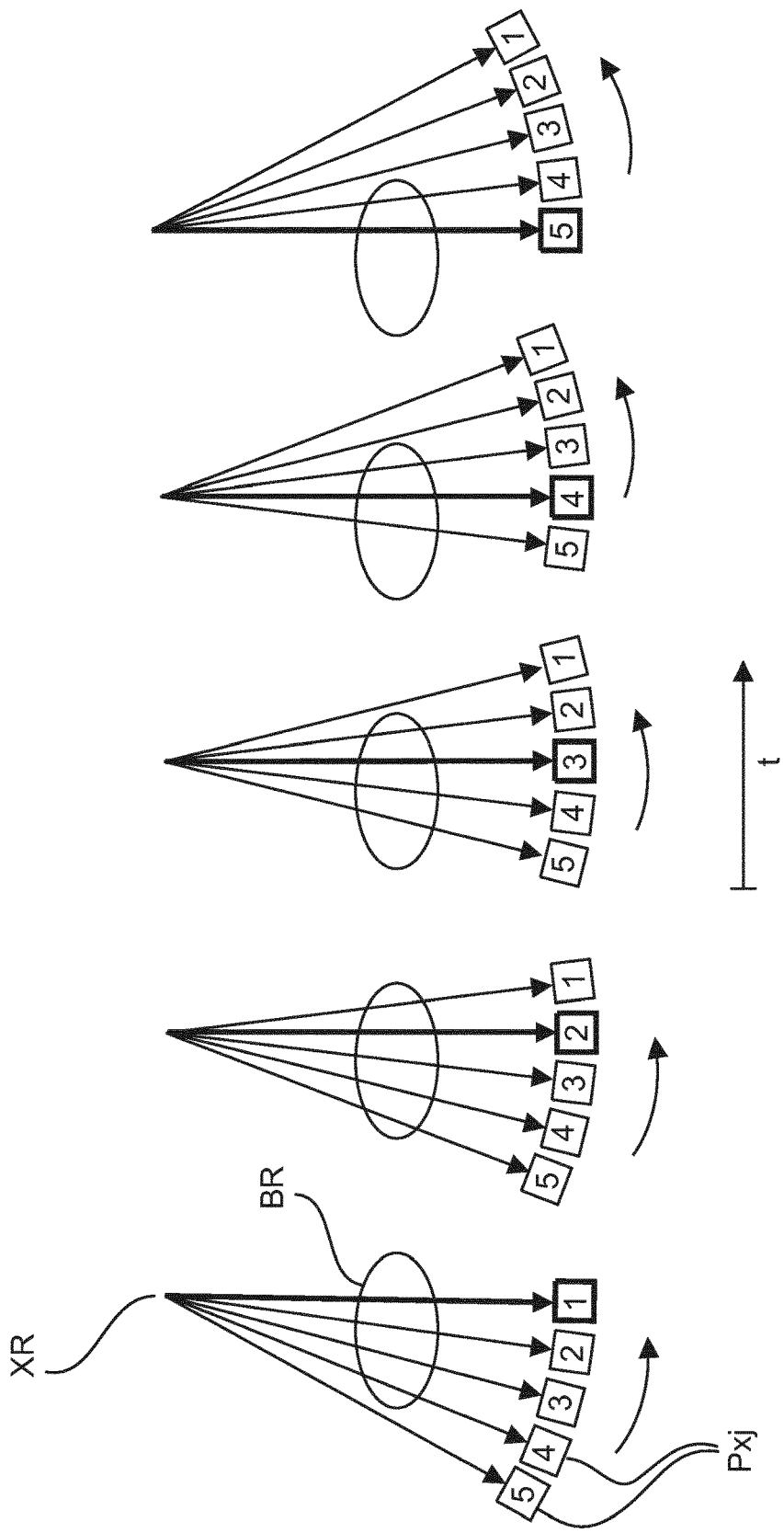
FIG. 2 shows a scanning operation of the imaging arrangement of FIG. 1.

FIG. 2 schematically shows the inherent redundancy (which equals the number of detector lines being on the order of 20 in one embodiment) in the multi-slit scanning approach. The detector lines (numbered 1-5) extend into the paper plane transverse to the scanning direction. By "readouts" as used herein is meant data collected by pixels along a given detector line when said detector line is at a given position l on the scan path. Put differently, the readouts are per detector line position. Note that the detector lines are drawn as distinct well separated lines in FIG. 2, but the lines can also be part of a contiguous 2D pixel array.

The local position of each pixel or line can be specific by two "coordinates", column or line index and the pixel index. Because the pixel width, inter-pixel and inter-line distances are known and so is the position of the detector plate at any instance on its path SP, each detector readout (that is pixel response) can be "spatially stamped" by a tracker (not shown) so each detector readout can be associated with a specific, fixed geometrical ray that can be thought of to extend from the focal spot FSP across the examination region to the detector plate D. There is a plurality of such geometrical rays, and to each point in the examination region there is such a geometrical ray that passes through said point the plurality of rays forming a cone with the focal spot FPS as apex. One such geometrical ray is shown in FIG. 2 in bold. The spatial stamps associated with the readouts allow identifying this redundancy.

The above described redundancy emerges also in the embodiment with fixed detector and movable interferometer where per detector pixel multiple readings are acquired for different positions along the scan path of the interferometer grating.

The present mammogram apparatus uses phase contrast imaging in other words the contrast of the images produced by a said imager do not rely solely on attenuation as is the case for conventional x-ray systems, but also relies on contrast that results from phase shifts which the radiation wave front experiences when interacting with the matter in the breast. The phase shifts or wave distortions are caused by locally different refractive behavior of the imaged matter. Another source of contrast of interest herein relates to small angle scatter (dark-field imaging) caused by microstructures.

However, the phase shifts themselves cannot be detected by the detector due to a lack of sufficient spatial resolution. Instead, the phase shifts and scatter contributions are derived indirectly by using the interferometric gratings to sample a spatial pattern, a Moiré image pattern that is, detectable after proper setup along detector lines. Moiré patterns occur when the periodicity of the interference fringes is slightly different from the periodicity of the structures of the analyzer grating G2. This is the approach taught by A. Momose et al in "High-Speed X-ray phase imaging and X-ray phase tomography with Talbot interferometer and white synchrotron radiation" in Optics Express, Vol 17, No 15, pp 12540, (2009). First, as a function of the average wavelength of the radiation emitted by source XR and suitably chosen respective periodicities p0, p1, p2 of gratings G0-G2, collimators and gratings are carefully tuned in respect of the detector lines to a desired Talbot distance of desired order by aligning in orientation and distance. See for instance, see T. Donath et al in "Inverse geometry for grating-based x-ray phase-contrast imaging," J. Appl. Phys. 106, 054703 (2009). By then carefully de-tuning this Talbot set-up, for instance by varying the distance between the source grating G0 and the π-phase grating G1 (or π/2-phase grating) a reference Moiré pattern emerges along the detector lines during a blank scan. How this reference Moiré pattern is detected depends on the local characteristics of the various detector pixels as will be explained in more detail below in connection with the calibration data. The proposition is then, that an intervening object BR in an object scan will disturb this Moiré pattern. The disturbance shows as a phase shift of the Moiré pattern and this Moiré pattern phase shift is known to be related to the local gradient of the phase shift experienced by the wave when passing through object BR. So we need to know the phase ("reference phase") of the Moiré pattern to be able to perform interferometric reconstruction, in other words phase retrieval alongside dark-field signal retrieval and attenuation retrieval. The Moiré phase reference and reference visibility is determined by processing blank scan data as will be explained in more detail below at eqs (2) and (2a).

In previous phase contrast imaging approaches, a fixed interferometric set-up has been used wherein, for phase retrieval purposes, one of the gratings is moved relative to the other to sample an interference pattern by "phase stepping". See for instance T. Weitkamp et al in "Optics Express", vol 13, No 16, pp 6296-6304 (2005). However, in the present approach no such phase stepping is needed. Instead, the phase retrieval operation is based on the scanning motion (together with the gratings motion) that is used herein to analyze the Moiré pattern fringes as recorded by detector during its motion to derive desired phase contrast information (and, incidentally, also the attenuation and/or dark field image which may be of use). So the detector motion serves to functions: first, it allows obtaining the full field of view this was the original purpose—and second, the motion is harnessed for phase retrieval purposes.

However, the redundancy in the readouts adds a layer of complication. Because of the scanning motion, the Moiré pattern is not only distributed in space along a detector line but is also distributed in time across the various detector readouts from different positions along the path. In DPCI or dark field imaging, the desired information of beam attenuation, beam refraction, and small angle scattering is obtained by the analysis of detected x-ray intensities along the same geometrical ray measured by different detector pixels (which have different relative grating positions of the Talbot interferometer G1-G2 in front of them). With reference to FIG. 2, data acquisition with a DPCI scanning geometry is illustrated: radiation along one particular geometrical ray (shown in as a bold sold vertical line) is measured during the scan by different detector pixels (of different lines) thus introducing a redundancy. The plurality of geometrical rays in the field of view of the imager "map out" different image pixel positions in the imaging region (or image space) from which the final image is made up. In other words there is 1:1 relationship between image pixel position and geometrical ray. In the view afforded by FIG. 2, the detector lines (numbered '1'-'5') extend into the paper plane.

The interferometer INF (that is, the system of gratings G0 and at least one of G1 or G2) in front of the detector pixels (when viewed from the x-ray source) is so tuned such that a full period of the Moiré pattern is sampled if all detector pixels are considered. To ensure this is the case, the mammography apparatus MA includes in one embodiment mechanical means, an adjustable rigidizer as it were (not shown), to be able to control the rigidity in particular of the scanner arm AR and some or all the gratings mountings GM by suitable mechanical action. A clamp like mechanism may be used for instance to act on the mounting means, e.g. a frame, that holds the gratings G1 and G2 in place. In another embodiment, bimetallic foil is used. One side of said foil is attached by bonding to the arm AR, either one the inside or outside. The arm is essentially (at least partly) "wrapped" in or lined with said foil. The bimetallic metal is then heated to various temperatures (before the scan due to account for a certain thermal inertial) which will then either increase or decrease the susceptibility of the arm to bending due to changes in gravitational torques during the scan.

One type of processing of the measured detector pixel data (essentially intensity values $m_i$) is based on the following sinusoidal signal model for the intensities $M_i$ of all pixels related to the same geometrical ray:

$$M_i = I_i A(1 + V_i D \cos(\phi_i + \alpha)) \quad (1a)$$

wherein:
- $m_i$: measurement data as seen at detector pixel i
- $I_i$: blank scan intensity of pixel i
- $V_i$ blank scan visibility of pixel i
- $\phi_i$: blank scan phase of pixel i
- A: attenuation factor
- D: dark field factor
- α: phase shift For reconstruction, the model is used to form a cost function $$\Delta j = \Sigma_i w_i (m_i - I_i A(1 + V_i D \cos(\phi_i + \alpha)))^2 \quad (1b)$$

where $w_i$ is a statistical weight (i.e., in one embodiment, the inverse variance of the measurement $m_i$). In one embodiment the formulation as per eq (1b) is basically a weighted least squares cost function that penalizes differences between the actually measured intensities $m_i$ and the expected intensities $M_i$ of the model. The statistical weights are variance estimates for the measured intensities $m_i$ (if this estimate is available) or are, in other embodiments, all unity. The weighted least squares cost function is appropriate if the noise in the data is Gaussian. For Poisson noise, a negative Poisson log-likelihood is appropriate.

Cost function (1b) is minimized to estimate the object parameters A, D, and α based on the measurement data $m_i$ (essentially a set of intensity values) and a set of interferometric reference parameters. The optimizing is essentially a curve fitting procedure based on least squares or any other suitable numerical method. This curve fitting will be referred to hereinafter as interferometry reconstruction or simply as "reconstruction".

The purpose of optimizing (1) is to "explain" the observed intensities $m_i$ by attributing the cause for said intensity partly to three different types of physical effects: attenuation, (small angle) scattering (loss of visibility) and refraction (shift of phase of wave front). The respective "strength" of the these effects are then quantified by the parameters or factors of best fit (per image pixel) as A, D, and α which each encode these strengths as "contrasts" to together then form the respective images: attenuation image, dark-field and phase-contrast.

The interferometric reconstruction as outlined above for equation (1) corresponds to processing the measurement data in object scan mode, that is, the measurement data is collected in the scan whilst the object resides in the examination region. The set of interferometric reference parameters (that is, blank scan intensities $I_i$, blank scan visibilities $V_i$, and blank scan phase $\phi_i$) represent the reference Moire pattern when there is no object interacting with radiation wave front. The introduction of the object then disturbs this reference Moire pattern and by optimizing (1) given the interferometric reference parameters one then arrives at the interferometry parameters of interest A, D, and α that quantify this disturbance as contrast values for the respective physical effect. The reconstruction of A, D, and α as per equation (1) above may be referred to herein as "reconstruction in object scan context" which is different from how the measurement data are processed that are collected during a blank scan. First, when reconstructing in object scan context as per (1), the interferometric reference parameters are assumed given whereas the purpose of processing measurement data collected during a blank scan is to precisely compute said interferometric reference parameters. Second, in object scan context reconstruction, one processed per geometrical ray j and not per detector pixel i. That is, for (1) the grabber or other data filter mechanism operates to first group all pixel i that contributed to the given image pixel (=corresponding to a certain geometrical ray) j and it is only those detector pixels that are considered in (1). In other words, the summation in (1) runs only over those pixels that have detected ("seen") respective measurements at image pixel (position) j. Optimization as per (1) is then repeated for each image pixel j. The different detector readings for given image pixel j can be obtained by scanning the detector or by scanning part of the interferometer INF.

The processing is fundamentally different when reconstructing for the interferometric reference parameters given blank scan measurements where now processing is per detector pixel or detector line and no longer per image pixel j. This type of reconstruction may be referred to hereinafter as "reconstruction in blank scan context". It is based on the following variant of model function (1a):

$$M_k = I_i(1 + V_i \cos(\phi_k)) \quad (2a)$$

This time the index k runs over different reading instances (that is, different positions on the scan path of the detector or part of the interferometer) for the same detector pixel i or detector line. As the incoming beam intensity $I_i$ and the visibility $V_i$ do not change with the readout position, these parameters can be obtained by minimizing cost function. (2b), see below. The blank scan phases $\phi_k$ can be obtained by analyzing the fringe pattern. Again the corresponding different readouts $m_k$ (i.e. the actual measurements) are collected by a grabber or similar filter, now clocked to pick up measurements $m_k$ at different scan path positions k (that is, detector or interferometer position). Optimization per detector pixel is otherwise similar to (1b) using least-squares methods or similar and processing to minimize the following cost function:

$$\Delta_i(I_i, V_i) = \Sigma_k (m_k - I_i(1 + V_i \cos(\phi_k)))^2 \quad (2b)$$

is repeated for each detector pixel position i, wherein one or more (in particular all) terms to the right of eq (2b) may depend on i.

It has been observed by Applicant that the interferometric scanner set up as described above in combination with a number of physical effects leads to the observation that the physical reference parameters for each detector pixel or detector line are different. More specifically, and referring back to the scanning operation as shown with further reference to FIG. 2, one may appreciate that physical (reference) parameters (explained in more detail below) for different ones of the geometrical rays are very likely not exactly the same: the geometrical rays are illuminated at different fan angles as seen from the tube XR, they pass the source grating $G_0$ at different angles, they also may pass the interferometer gratings $G_1$ and G2 at different angles. All these variations accumulate in a slight variation of the initial beam spectrum. The problem that arises in this situation is that the beam is attenuated slightly differently for each detector pixel by the object BR. If this effect is not taken into account, the additional variation of detected signal will be—at least partially—attributed to a change in visibility or a phase shift of the Moiré pattern. Thus, the ultimate consequence is the appearance of beam hardening artefacts because of the functioning of the above described reconstruction algorithms as per eqs (1), (2). Another effect of the described situation is that the fringe visibility changes differently for different pixels since the visibility is a complex function of the spectrum. Again, if not taken into account, the effect leads to artefacts in the reconstructed images, in particular to beam hardening artifacts. In sum, due to various physical effects, slight variations of the x-ray beam spectrum occur (this is the beam hardening effect), which variations are amplified differently by each pixel, thereby causing artifacts in the phase contrast or dark-field image.

Therefore, to remove or at least mitigate beam hardening artifacts in phase contrast or dark field imaging, it is proposed herein a signal processing sub-system SPS that includes a beam hardening processing component BHC in corporation with a interferometric re-constructor RECON.

Briefly put, the imager MA operates to acquire measurement data obtained in an object scan when scanning an object (for instance, the breast BR) one wishes to image. The SPS then collects all the measured intensities obtained in the object scan that correspond to a given geometrical ray. The data is said to "correspond" to the geometrical ray if they contribute to the image pixel signal for said ray. The data $m_i$ per geometrical ray as detected by the detector during the object scan is then received at input port IN. The system SPS then performs collectively a beam hardening operation for those contributing intensity values. The beam hardening operation, per geometrical ray (or equivalently, image pixel position) includes in particular computing for those contributing intensity values correct interferometric reference parameters (which includes in particular reference intensity I and the reference visibility V) in which numerically, the beam hardening effects have been adjusted for. Those corrected interferometric reference parameters are computed to fit the actual attenuation experienced by the radiation along said ray. To do this, the proposed beam hardening processing component BHC uses a "lead variable" referred to herein also as an "indicator variable" that "indicates" or relates to the attenuation experienced by the beam along said ray. This information about the mean attenuation experienced along said ray is then used as a "guiding stick" to compute the corresponding reference intensities and/or invisibilities. This computation can be achieved in one embodiment by obtaining an estimate for the indicator variable and applying same to an a-priori known functional expression (derived from a signal model) that encodes the correct functional relationship between the attenuation and the intensities and/or the visibilities. In one embodiment, rather than using a (closed or iterative) analytic expression, a more experimental approach is taken, tailored to the particulars or characteristic of the given imaging apparatus. In other words, calibration data is obtained from the imager by using a specifically designed, dedicated phantom body and the calibration data is then processed in a manner to be explained in more detail with reference to FIG. 8 to obtain two or more look-up tables through which the fitting visibilities and intensities can be looked up that correspond to the mean attenuation experienced along the ray. In other words, in this embodiment, the computation of the corrected reference parameters reduces to a simple look up operation. Once the correct reference parameters are gotten, the system SPS then proceeds to feed same into the interferometric reconstructor RECON to reconstruct (based on the measured data) in object scan mode for the beam hardening corrected phase contrast and/or dark-field image. The reconstructed data of the beam hardening processing can then be output through output port OUT and can then be viewed on the monitor MT or stored in a data base or otherwise processed.

In the embodiment where the beam hardening operation rests on calibration data, the signal processing component SPS includes a calibration component CALC that effectively co-ordinates processing by the reconstructor to reconstruct the measured data in object scan context and/or blank scan context as explained above. In other words the calibration component CALC instructs the re-constructor to process the received measurement data as if it obtained in a blank scan and then to again process the same data as if it were obtained in an object scan. The so "doubly-reconstructed" data is then organized as calibration data in look-up table structures or other suitable data structures which are then stored in a data base DB. They can then be accessed by the beam hardening processing module BHC for any given measurement data.

The signal processing component SPS can be integrated into the circuitry of the detector electronics or can be run as a software module on a workstation WS or operator console associated with the imager MA.

Reference is now made to FIGS. 3-6, 8 and 9 where more details are shown for the embodiment where a phantom body PB is used.

Figure 9:
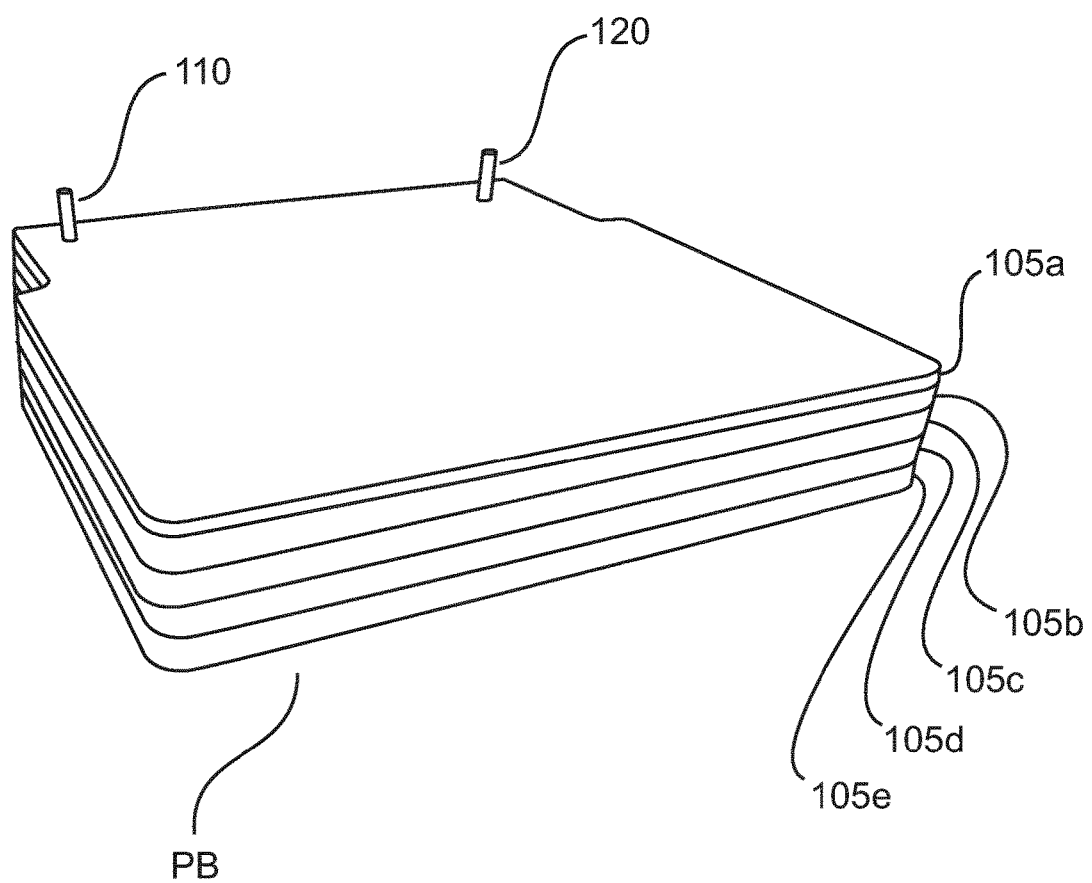
FIG. 9 shows a phantom body of variable thickness according to one embodiment.

FIG. 9 shows one embodiment of such a phantom body PB envisaged herein. Broadly, the phantom body is configured so that its material thickness can be adjusted in discrete steps. This can be achieved in one embodiment as shown in FIG. 9 by having the phantom body arranged as a plurality of slabs 105a-105e of a homogenous material such as polycarbonate (also known in the trade as Lucite) but other materials are likewise envisaged. The slabs 105a-105e are sized so as to cover preferably the entire field of view of the imager MA. In other words, shape/size of the slabs will depend on the particular geometric constraints of the fields of the examination region of the imager MA to be used. As can be seen in the specific embodiment in FIG. 1, in FIG. 9 the slabs are essentially rectangular with a tapering at one of its ends to account for geometrical space constraints. In its simplest embodiment the phantom body simply consists of a set of two, three, or more, in particular five, slabs each having the same thickness, for instance 1-2 cms. However, other thicknesses are also envisaged and the slab thicknesses may not be the same but all or some of the slabs may have different thicknesses.

According to one embodiment the phantom body set includes fiducials to assist in precisely stacking the slabs when increasing the phantom's body thickness.

As shown in FIG. 9, in one embodiment the alignment fiducials are realized as a peg-hole system. One of the slabs has two or more pegs 110,120 extending therefrom upwardly. In some or all of the remaining slabs, through-holes are formed. The through-holes correspond in number, shape and size to the pegs 110,120 to safely register with the pegs 110,120 to achieve precise alignment. Other embodiments for the fiducial system are also envisaged herein. For instance, rather than having a peg-through-hole arrangement, one side of each slab may be furnished with protrusions extending away from the face of the respective slab, the protrusion having in general a smaller height (less than the thickness of the thinnest slab in the set) than the pegs in the embodiment described earlier. The protrusions are suitable distributed across one face of each slab, for example one protrusion for each corner assuming a rectangular slab shape. The opposing face on the other side of each slab includes corresponding depressions (but not through holes) or "dimples" to receive the protrusions of the neighboring slab to be placed on top or under it. The protrusions and recesses are formed for snug registry when placing the slabs on top of each other. Some minor "exploratory" sliding motion by the user will ensure that the protrusions eventually engage their respective depression in the neighboring slab to thereby achieve the desired alignment.

In another embodiment of the phantom body PB, the plurality of slabs is arranged in a "Swiss pocket knife" fashion. In this embodiment the slabs 105a-105e are adjoined to each other at a common pivot point like the blades in the knife and the respective slices can then be swung in or out of the field of view as desired so as to build up or decrease in steps the thickness (or "height") of the phantom body PB. An auxiliary support structure may be required to ensure balanced support. In another embodiment, which may be referred to herein as the "chest drawer" embodiment, the slabs are independently horizontally slidable in a frame structure. The slabs can be slid in or out the frame and into the examination region to so combine the slabs into the desired thickness or height. Alternative, in a very simple embodiment, the phantom PB may be formed from a single slab which may be useful in some instance as will be explained below at FIG. 9.

Figure 3:
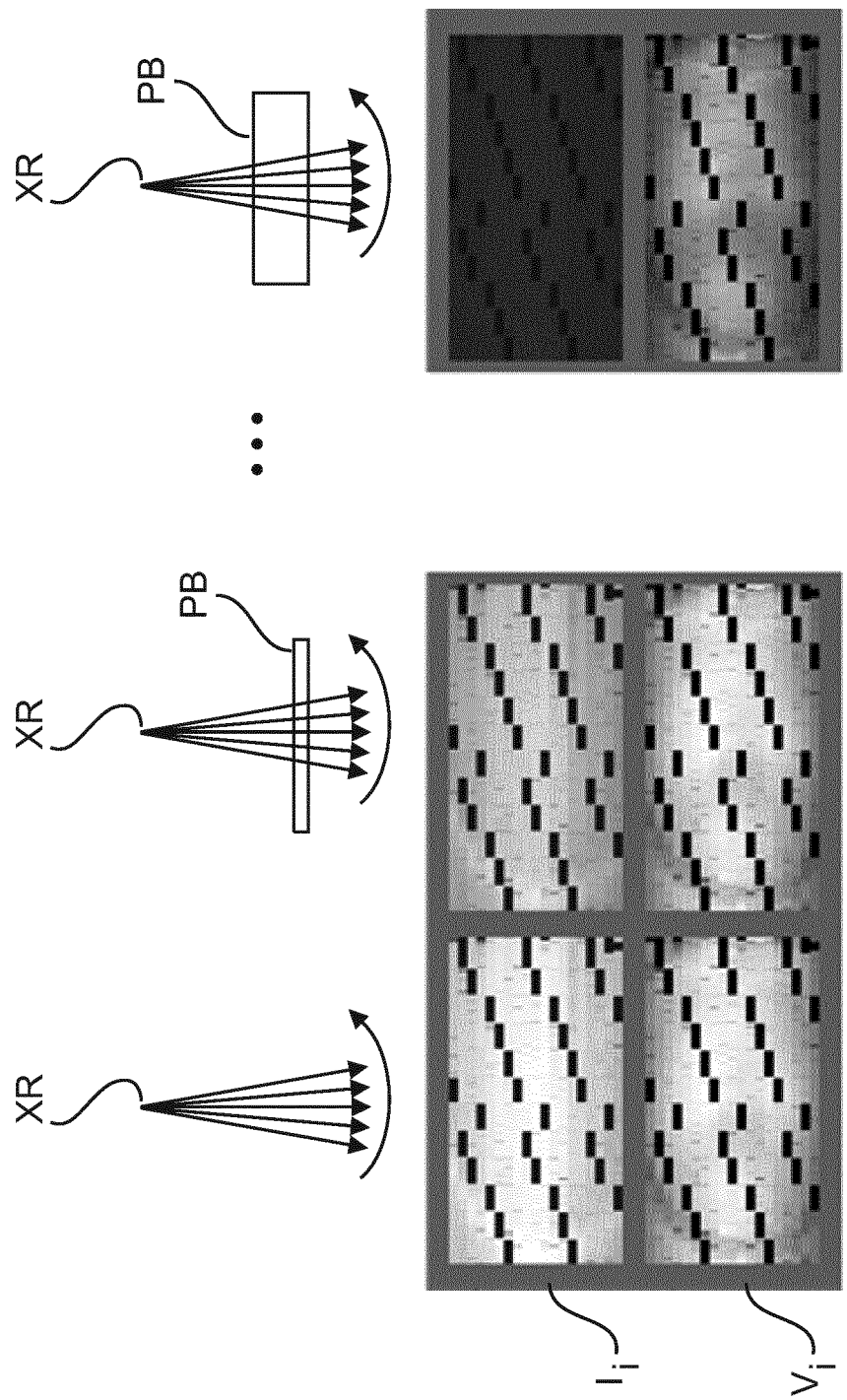
FIG. 3 shows diagrammatically a scanning phantom body of different thicknesses and processing the respective detector readout as blank scans.
Figure 4:
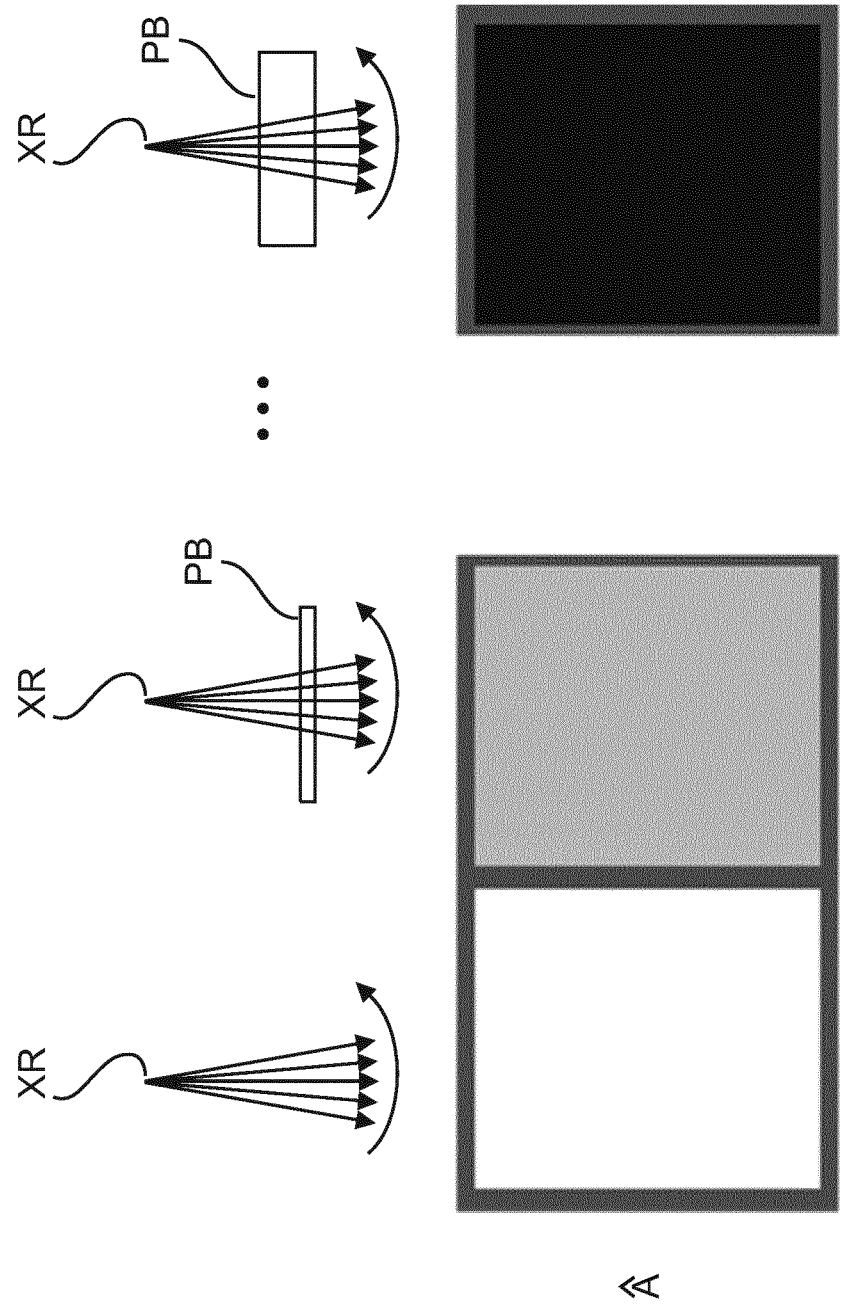
FIG. 4 shows diagrammatically a scanning of a phantom of different thickness and processing the respective readouts as object scans.

FIGS. 3 and 4 show how the phantom PB is to be used in one embodiment.

In FIG. 3, the phantom's thickness is gradually built up and for each given thickness a set of scan measurements are acquired by scanning the detector as described above. The very left of FIG. 3 shows a blank scan where no phantom body is arranged in the examination region and to the right thereof instances are schematically depicted where the phantom's thickness is gradually increased with respective detector readouts acquired. For illustration, the detector readouts are graphed for a particular geometric ray as a function of the respective detector line passing the respective geometric ray. The black bars in the detector readout are owed to the fact that the detector lines in general are not arranged as continuous lines but have gaps in between. However, other embodiments may be envisaged where detector lines are arranged continuously with no gaps. The detector readouts acquired in FIG. 3 are then each processed in a blank scan context, that is, an interferometric reconstruction is performed for each pixel and each detector line. In other words, rather counterintuitively, although there is an object (that is, the phantom PB) in the examination region, the acquired measurement data is still processed in blank scan context. This blank scan processing (as per eq (2b)) then results in intensity I and visibility maps V which can be stored in a look-up table in association with the respective phantom thickness or more particularly path length or equivalently the average mean attenuation experienced by the beam. The later can be readily computed from the known path length and the known attenuation properties of the phantom material (in this case polycarbonate but other materials are also envisaged herein).

In FIGS. 3, 4, and 9, the slabs are shown as being planar which may be useful for applications where the scan path is straight or has small curvature. However, in other embodiments, in particular with arcuate scan paths of appreciable curvature, a correspondingly curved form for the slabs is preferred. In other words, the slabs 105a-e are formed according to respective parts of (imaginary) concentric cylindrical surfaces with the center of the cylinders being located in the focal spot of the source XR so that the ray length/through the object remains constant during the scan.

As per FIG. 4 the acquired detector readouts are now processed as object scans. In other words, an image pixelwise (geometrical ray wise) reconstruction is performed to reconstruct the three interferometric quantities, of which now the mean attenuation is retained as the reference parameter as a parameter of interest. The blank scan information obtained in the processing as FIG. 3 can be used for the object scan processing in FIG. 4.

The object scan processing of the acquired detector readout for each phantom thickness allows precisely correlating the theoretically to be expected attenuation across the phantom with the actually computed attenuation (as one of the three interferometric quantities that is yielded interferometric reconstruction of FIG. 4). The theoretical beam attenuation and the actually computed interferometric attenuation can then be stored again in association in a second look-up table.

Figure 5:
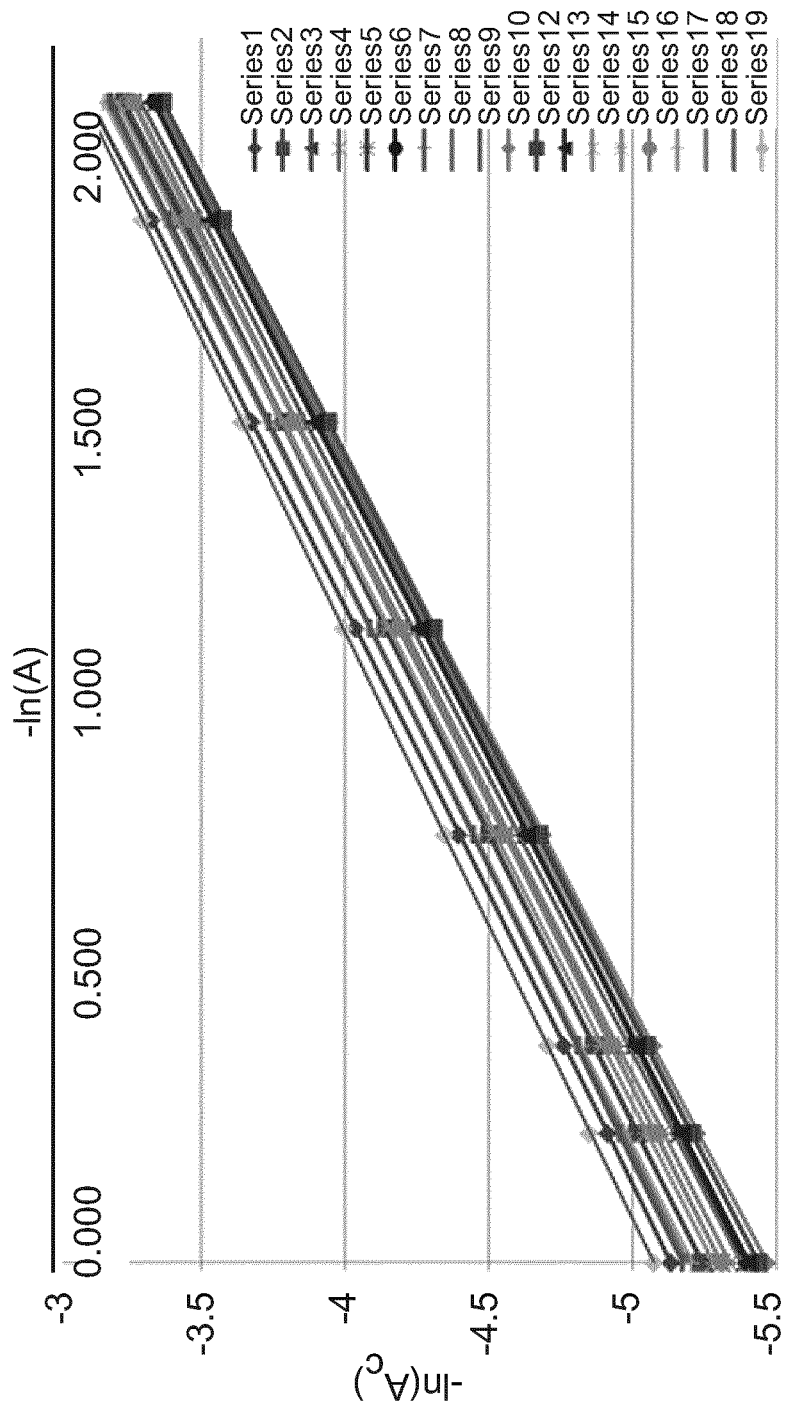
FIG. 5 shows a look-up table of intensities detected at a detector versus beam attenuation for different detector lines.
Figure 6:
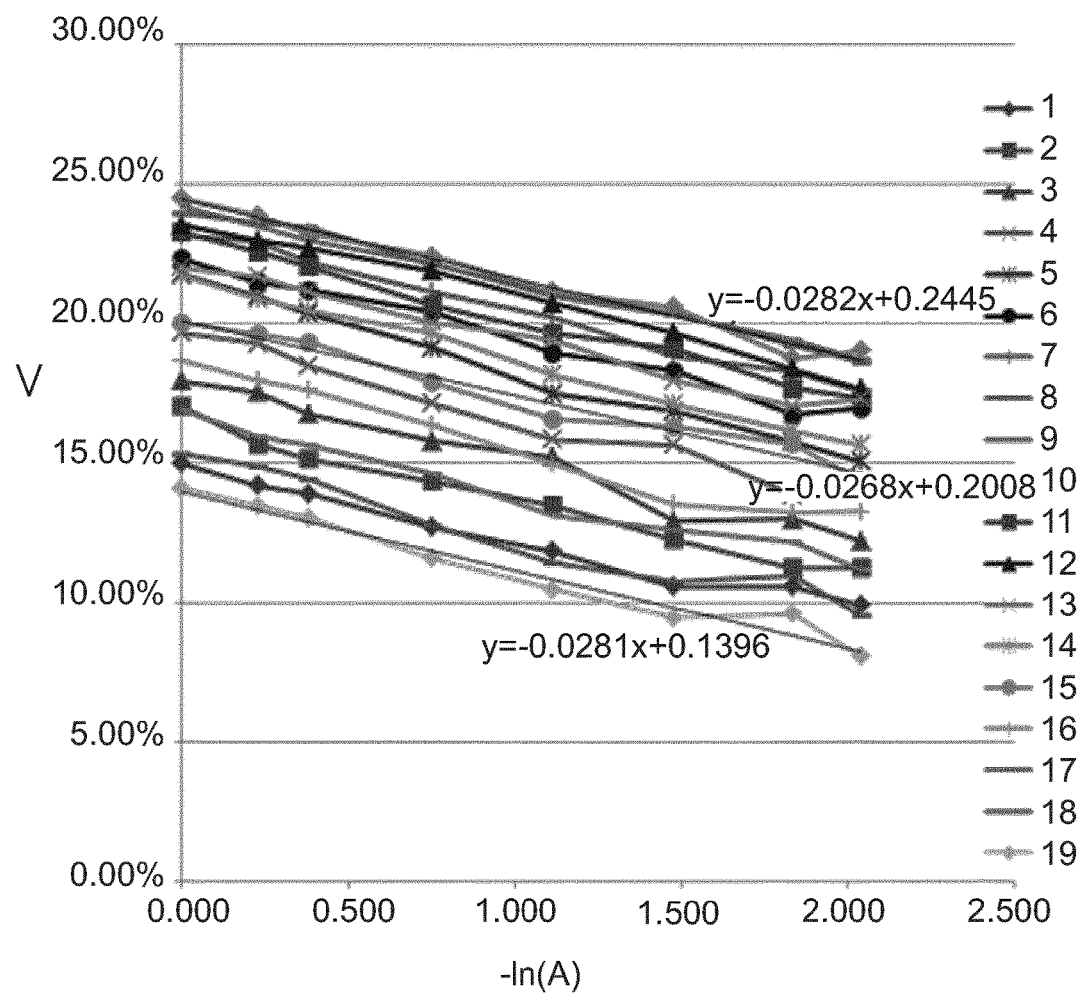
FIG. 6 shows a look-up table that shows for each detector line measured beam attenuation versus fringe visibility.

Respective look-up tables for the intensities and visibilities as per FIG. 3 and the attenuations as per FIG. 4 are illustrated in FIG. 5 and FIG. 6, respectively.

In FIG. 5, for each measured mean beam attenuation A (x-axis), a first LUT provides the correct mean detector measurements (e.g. "counts", when a photon counting detector is used but this is not limiting as more conventional detectors of the energy integrating type are also envisaged herein in alternative embodiments) for each detector line for this beam hardening level. This "attenuation-LUT" obtained from the processing as described above and illustrated in FIG. 3, allows to look up for each reconstructed mean beam attenuation (i.e., for each beam hardening level) the correct mean intensity of the Moiré pattern for each detector pixel. Since attenuation is an exponential process, it is advantageous to store the LUT in logarithmic values for the input and output of the data and this form of storing is envisaged herein in some embodiments.

As per FIG. 6, for each measured mean beam attenuation A (x-axis), a second LUT provides the correct fringe visibility $V_c$ for each detector line for this beam hardening level. This "visibility-LUT" allows to look up for each reconstructed mean beam attenuation (i.e., for each beam hardening level) the actual visibility for each detector pixel. Again, since attenuation is exponential, the x-axis of the LUT is preferably logarithmic. However, the change in visibility as a function of amount of beam-hardening seems to be well described on a linear scale. The LUT(s) may be formed for each detector line as a whole or for each detector pixel individually (preferred).

As can be seen in FIGS. 5 and 6, the respective functional relationships between the visibility and the attenuation is different for each detector line. The look-up table is essentially a multi look-up table, one for each detector line or even each detector pixel. In other words, for each detector pixel line there is a slightly different functional dependency of I and V on the attenuation. Interestingly, it has been found that the functional dependency as can be gathered from the LUT in FIG. 5 and FIG. 6 in particular is essentially linear with a different slope for each detector line. It can be seen that the look-up tables as per FIGS. 5 and 6 gathered from the calibration procedure as outlined in FIGS. 3 and 4 can be advantageously used once an estimate for the mean attenuation is available in the form of an indicator variable as indicated briefly above. For instance, the average path length through an object to be imaged or an estimate for the mean attenuation itself can be used to look up in the tables the corresponding visibilities and intensities to thereby compensate for the beam hardening otherwise incurred if one were to run a standard reconstruction of the three interferometric quantities.

For instance in one embodiment one may run a two stage processing: one may run a first interferometric reconstruction based on object detector readings to obtain (as previously described in literature) the three interferometric quantities: attenuation signal, phase contrast signal and dark field signal. For this first reconstruction, an initial set of interferometric reference parameters are used previously obtained in an initial standard blank scan. The dark field signal and the phase signal are for a moment disregarded herein and the reconstruction attenuation is used as an indicator variable to look up for each detector pixel the corresponding reference intensity and visibility. This allows ascertaining for each detector pixel the correct reference parameters adjusted for the beam hardening effect. It is these reference parameters (together with the phase reference parameter from the initial set) that are then used to run a second interferometric reconstruction from the measured detector readings to thereby arrive at beam hardening corrected interferometric quantities of interest, in particular the phase contrast and dark field signal.

Figure 7:
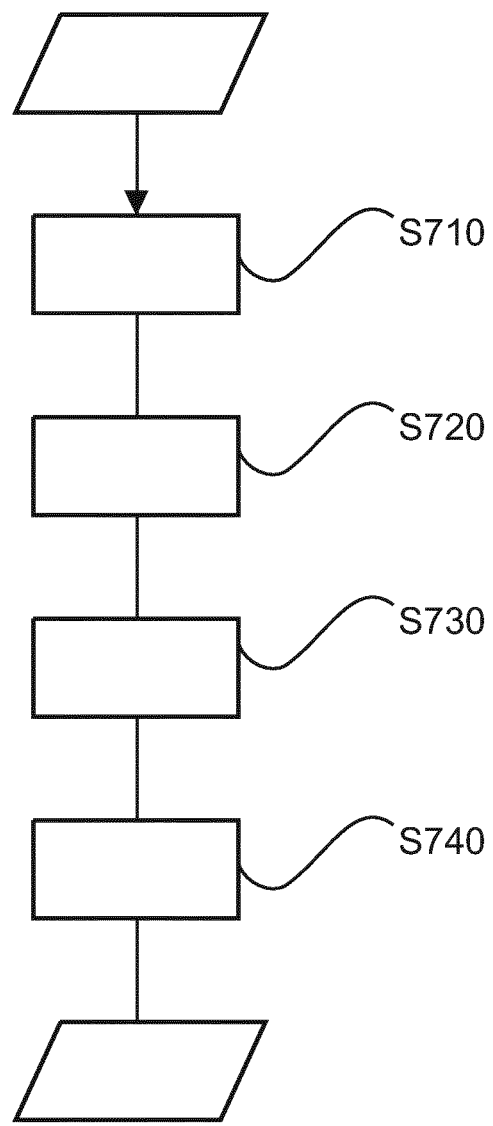
FIG. 7 is a flow chart of a method processing detector data as supplied by a phase contrast or dark field imager.

The following flow charts in FIG. 7 show steps of a method for processing interferometric detector readings supplied by a grating based differential phase and/or dark field signal imager, whereas FIG. 8 below shows steps of a calibration procedure using a height or thickness adjustable calibration phantom body.

Referring now first to FIG. 7, at step S710 detector readings from a scanning imaging system with an interferometer is received in the form of intensity values. The intensity values are grouped by a filter mechanism (such as a data grabber) into respective groups of intensity values that belong to a respective image pixel position.

At step S720 for each image pixel position, a least a part of a beam hardening correction operation is then performed in respect of those intensity values that belong to that image pixel position. The beam hardening processing operation includes computing as a function of an indicator parameter, interferometric reference parameters which can be used in a subsequent interferometric reconstruction (see step S730 below). The interferometric reference parameters include in particular reference intensity and a reference visibility for the given image position that belongs to image pixel position under consideration and the so computed interferometric reference parameters are computed so that beam hardening effect are adjusted for. Step 720 is then repeated for each image pixel position.

In one (but necessarily all embodiments), step S720 is two-stage: first, as standard (i.e. without beam-hardening correction) interferometric reconstruction is performed to obtain a possibly beam-hardening corrupted estimate Â for the beam attenuation as the indicator parameter. Next, the possibly beam hardening corrupted, estimate Â is used to look up the correct values for the beam intensity and visibility for this beam-hardening level for each detector pixel that contributes to this ray.

At step S730 an (in one embodiment a second, that is a new) interferometric reconstruction is then applied to said intensity values (for said geometrical ray) and the reference parameters obtained from the beam hardening operation to obtain a phase contrast signal and/or a dark field signal. These signals then have the beam hardening correction removed or at least mitigated.

Lastly, the obtained value A for the beam attenuation is multiplied with the initial estimate Â since the interferometric reconstruction provides a change compared to the beam hardened calibration scan.

The so reconstructed phase contrast signal and/or dark field signal are then output at step S740 for further processing.

In the two-stage embodiment of step S720 above, the indictor variable is an estimate (form the first reconstruction) of the mean beam attenuation but in other embodiments the indicator variable may be expressed in terms of path length for instance, or any other suitable surrogate, that is, in some embodiments the mean attenuation may not need to be computed explicitly. The entries of the LUT and the interferometric reconstruction model equation may then need to be reformulated in terms of said surrogate indicator variable. For instance, when the path length is used, the previous model equation (1a) may be reformulated as:

$$M_i = I_i(l)(1+V_i D \cos(\phi_i + \alpha)) \quad (3a)$$

leading to the corresponding cost function to minimize in order to obtain estimates for the object parameters l, D, α:

$$\Delta(l,D,\alpha) = \Sigma_i (m_i - I_i(l)(1+V_i D \cos(\phi_i + \alpha)))^2 \quad (3b)$$

A similar surrogate reformulation may be applied instead or in addition to the visibility. For instance, it has been found that the visibility is essentially a function of beam hardness and thus the path length through the object may be used as a surrogate. If both attenuation and visibility is reformulated in path length terms, the model equation may be written as:

$$M_i = I_i(l)(1+V_i(l)D \cos(\phi_i + \alpha)) \quad (4a)$$

leading to a corresponding cost function as per.

$$\Delta(l,D,\alpha) = \Sigma_i (m_i - I_i(l)(1+V_i(l)D \cos(\phi_i + \alpha)))^2 \quad (4b)$$

It is however advantageous to use the attenuation itself as the indicator variable because this has been found to reduce the computational burden in the fitting procedure.

As mentioned earlier, the proposed method does not rely on the LUTs and calibration data to compute the beam hardening corrected interferometric reference parameters from the indicator variable (which is either the attention itself or a surrogate thereof). Instead, the beam hardening processing at step S720 can be applied by using a known analytic expression that captures or encodes the functional relationship between the visibility and intensity versus the attenuation. In particular, the one or more interferometric reference parameters are computed as a function of an indicator parameter that is known to relate to the mean attenuation experienced by the radiation along that ray. If the path length is used as an indicator variable (as a surrogate for attenuation) the function relationship between visibilities and intensities respectively may have to be expressed as a more complex approximation, such as an approximation polynomial of degree d>1 or any other suitable analytic functional expression.

This indicator parameter may for instance be derived as an estimate for the mean attenuation from a previously executed interferometric reconstruction performed on the acquired detector data. However, the indicator variable parameter may also be supplied in the form of a surrogate for said mean attenuation, for instance the respective path lengths through the object to be imaged, if known, can be used instead for the computation. In fact, any other variable that is known to be deterministically (and preferably monotonically) linked to the experienced attenuation can be used.

In the previous two formulations as per eqs (3), (4), a physical model for the intensity I as a function of the object thickness l is $$I_i(l) = \int_0^{E_{max}} S(E) e^{-l\mu(E)} dE \quad (5)$$

where:—

S(E) is the product of spectral sensitivity of the detector D and the incoming x-ray flux (without the sample in the beam), $E_{max}$ is the maximum photon energy in the beam, and μ(E) is the energy dependent linear attenuation coefficient of a surrogate material (for instance water, PC, PMMA or alike).

Although functions $S(\bullet)$, $E_{max}$, $\mu(\bullet)$ can be calculated theoretically ab initio, it is often more convenient to establish a heuristic approximate model for these functions. For instance, in the calibration procedure as outlined in FIGS. 3,4 above involved the measurement for one or more slabs 105a-e of homogeneous material, and the processing provides therefore a list of measurements $I_i(l_j)$ for some discrete thicknesses $l_j$. These samples can be used to generate an approximate continuous function $\hat{I}_i(l)$ by appropriately interpolating between these samples. An interpolation function may be generated by cubic spline interpolation, by piecewise linear interpolation, or by fitting a low-order polynomial or rational function to the measured data.

The above described numerical approaches as per any one of equations (2)-(5) represent different operational modes of the beam hardening processing component BHC. In one embodiment (eqs (2)), BHC operates in, using the language of inverse problems, backward mode (eqs 2) as a corrector whereas operation as per eqs (3, 4) is more a kind of forward mode processing. In the latter case, the beam hardening processing step comes about as determining, individually per image pixel, beam-hardening compensated reference parameter (intensity and/or visibility) for the respective image pixels. These image-pixel-individualized reference parameter are determined as a function of the lead parameter which represents a property of the object BR (such as equivalent path length l through a known reference material (PC or other) or mean attenuation) which is not image pixel specific. With reference to FIG. 8 there is now shown a flow chart for a method of producing calibration data as explained above for the purposes of beam hardening correction in scanning phase contrast or dark field imaging.

At step S810, scans are performed with a scanning imager having an interferometer to acquire a plurality of different sets of calibration detector readings. The sets include one for a blank scan and one or more sets for a phantom body PD scan. The phantom body is configured so that its thickness or height is adjustable so that the detector readings in the different phantom scans correspond to different thicknesses of the phantom. The so acquired sets of calibration detector readings are then processed twice in different context as follows.

At step S820 the acquired sets of detector readings are processed each per detector pixel/detector line in an interferometric reconstruction operation to so derive an interferometric reference parameter for each detector pixel or line per blank scan and phantom thickness. In other words, both the blank scan data and the one or more phantom scan data, are reconstructed in blank scan context.

Optionally, at step 830 a second interferometric reconstruction is performed on the different sets of detector reading data, however, this time each of the data is interferometrically reconstructed per image pixel to obtain in particular an interferometrically reconstructed indicator parameter for the experienced mean attenuation level. Because the actual phantom thickness is known, the actual attenuation experienced can be directly linked to the so reconstructed mean attenuation. In other words, in step S820, all data sets obtained in the scans per step S810, even the blank scan data set, are reconstructed in object scan context. As explained earlier above in connection with eq (1), reconstructing in object scan mode requires reference parameters from a blank scan. The reference parameters obtained in step S820 for the blank scan can be used for the object scan context reconstruction purposes of instant step S830. Step S830 is used preferably if reconstruction is based on backward model formulation as per eq. 1b but can be skipped if reconstruction is based on the forward formulation as per equations 3b or 4b.

From steps S820 and S830 the respective reconstructed data can be organized in a look-up table or similar data structure so that to each practically known attenuation level, corresponding intensities or visibilities can be associated. In other words, the respective interferometric reference parameters as reconstructed in step S820 are stored in association with a respective indicator parameter that relates to the mean attenuation levels experienced and caused by the respective phantom thickness or the blank scan. As can be seen from the above, Applicant has discovered inter alia that the blank scan visibility is a function of the beam hardness, that is, is essentially a function of path length through the object.

Figure 8:
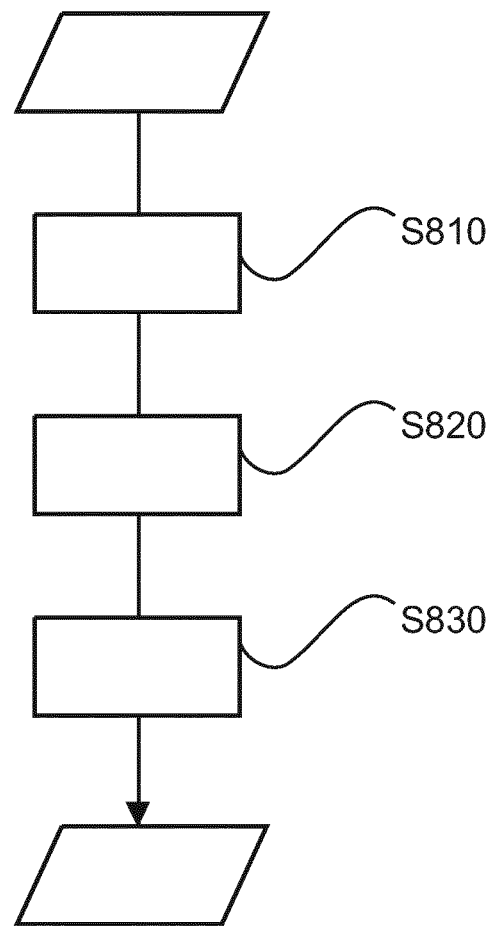
FIG. 8 shows a map for producing calibration data for beam hardening processing/correction in scanning phase contrast or dark field imaging.

Although the methods as per FIGS. 7 and 8 have been explained largely with reference to the embodiment where the detector (with the interferometer mounted thereon) is moved in the scan operation, each of the above is of equal application for the embodiment where the detector is fixed and it is the a part of the interferometer INF (that is, one and/or more gratings thereof) are scanned past the object. In particular, for this later embodiment, the index i in above formulations (1)-(5) indicates measurements $m_i$ at a given single detector pixel but for different positions of one or more gratings of the interferometer INF when passing said single pixel during the scan operation.

Applicant's tests have confirmed that the calibration tables hardly change over time, so that there will be no need to perform the above calibration procedure as per FIG. 8 more often than weekly.

In sum and according to one embodiment, the proposed method and system involves the use of a calibration phantom having an adjustable number of slabs of homogeneous material covering the entire field of view. More specifically, during a calibration phase, data are acquired with the phantom for different material thicknesses (i.e. different number of slabs). This data is processed, in one embodiment, in form of blank scans (eq 2b) and also in the form of object scans (eq 1b). Alternatively, when using forward processing as per eqs (4b), we can directly use the known thickness 1 as parameter and it is sufficient to process in the form of blank scans. Based on this processing, two lookup tables are built and stored: one for the attenuation and one for the visibility of the fringe pattern, for each detector pixel (or line). During imaging of a patient, standard phase retrieval provides a first estimate for the beam attenuation, which estimate is corrupted by beam hardening. For this estimate value, intensity and visibility values are retrieved from the look-up tables generated during calibration. Using these intensity and visibility values, a new phase retrieval is performed in which beam hardening is corrected for.

Applicant's tests have revealed that running the above described calibration scheme on a weekly basis is sufficient in particular for scanning mammography systems.

Some phase contrast or dark-field processing requires that the Moiré pattern drifts during the acquisition at least by one complete period of the fringe pattern. It has been observed that in these systems, the number of calibration scans can be reduced if one induces a stronger drift of the system during the calibration scans, which can be achieved by the rigidizer mechanism mentioned above.

The above described methods and signal processing system SPS may also be applied in CT context instead of projection radiography because beam-hardening effect may also cause artifact problems in phase contrast or dark-field tomography (CT). In fact, a very similar situation as in the mammography embodiment discussed above is in fact at hand in CT if the acquisition mode in tomography does not employ explicit phase stepping, or if phase information is spread over several detector pixels like in the moiré scanning of the sliding window technique. For these specific CT acquisition modes, an iterative reconstruction method that operates directly on the measured intensities rather than on the individual signal channels after interferometric reconstruction has been successfully been used. Specifically and according to current proposals the interferometric reconstruction for CT is based on the following signal model for the measured intensity I as a function of the attenuation image µ, the dark field image σ, and the phase image δ as $$I = I_0 e^{-\int \mu dx}(1 + V_0 e^{-\int \sigma dx} \cos(\phi_0 - \partial_x \int \delta dx)) \quad (6)$$

which contains for instance only a constant blank scan visibility $V_0$. Processing in CT context preferably uses an iterative reconstruction algorithm which includes formulating a suitable cost function in terms of model (6).

By a calibration measurement of the visibility after beam-hardening, the above model can be superseded by the model $$I = I_0 e^{-\int \mu dx}(1 + V_0(\int \mu dx) e^{-\int \sigma dx} \cos(\phi_0 - \partial_x \int \delta dx)) \quad (7)$$

where the reference visibility becomes now a function of the current amount of beam-hardening, represented by represented by the indicator variable, for instance the line integral of the attenuation contrast image µ. Equation (6) can be seen as an adaptation of eq (1) for CT context and the above described methods for projection radiography (e.g. mammography) can be readily applied to the CT context based on eq (7).

In one embodiment, some or all of the components of image data processing system SPS as per FIG. 1 are envisaged to all run a single computing system like the imaging apparatus' MA workstation WS. In an alternative embodiment an at least partly distributed architecture is likewise envisaged herein where one or more of the components are located remotely and are connected with each other and/or with the image data processing system IDP in a suitable communication network.

In one embodiment, image data processing system SPS (or at least some of its components) is arranged as a dedicated FPGA or as a hardwired (standalone) chip.

The components of image data processing system may be programmed in a suitable scientific computing platform such as Matlab® and may be translated into C++ or C routines suitable to run on a computing system (such as the imager's workstation WS).

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image signal processing system for processing data, comprising:
  a scanning radiography imager configured to provide the data, wherein the imager includes an x-ray source for emitting radiation, a detector for detecting the radiation, and an interferometer arranged at least partly between the x-ray source and the detector;

an input port for receiving data as intensity values that correspond to one and a same geometrical ray, the intensity values being acquired using different detector pixels of the detector in a scan operation by the imager of an object or using a respective single detector pixel while at least a part of the interferometer is moved past said single detector pixel in the scan operation;

a beam hardening processing component configured to apply, for a given image pixel position as per said geometrical ray, a beam hardening processing operation with respect to said intensity values, thereby obtaining at least one interferometric reference parameter including at least one of a reference intensity and a reference visibility for said image pixel position;

a reconstructor configured to reconstruct from said intensity values and said at least one interferometric reference parameters at least one of a phase signal and a dark-field signal; and an output port for outputting at least one of said phase signal and said dark-field signal.

2. The image signal processing system according to claim 1, wherein the beam hardening processing operation includes computing, for said intensity values, said at least one interferometric reference parameter as a function of an indicator parameter that relates to a mean attenuation experienced by the radiation along said geometrical ray or to a property of the object to be imaged.

3. The image signal processing system according to claim 2, wherein the indicator parameter comprises an estimate of a mean attenuation previously reconstructed from the received intensity values or a surrogate for said mean attenuation.

4. The image signal processing system according to claim 1, wherein a functional relationship between the indicator parameter and the at least one interferometric parameter is different for different ones of the detector pixels or the respective single detector pixels.

5. The image signal processing system according to claim 4, wherein the respective functional relationships are encoded as one or more look-up tables compiled from calibration data or as one or more functional expressions.

6. The image signal processing system according to claim 5, wherein the calibration data is derived from calibration detector readings acquired by the imager in a blank scan and at least one phantom scan for a given thickness of a phantom body or a plurality of phantom scans for a variable thickness of the phantom body.

7. The image signal processing system according to claim 6, wherein the phantom body has an adjustable thickness to achieve the variable thickness.

8. The image signal processing system according to claim 1, wherein the at least one reference interferometric parameter includes at least one of a visibility and an input intensity, per detector pixel or for said respective single detector pixel.

9. A method for processing data supplied by a scanning radiography imager having an x-ray source for emitting radiation, a detector for detecting the radiation, and an interferometer arranged at least partly between said x-ray source and said detector, the method comprising:

receiving data as intensity values that correspond to one and a same geometrical ray, the intensity values being acquired using different detector pixels of the detector in a scan operation by the imager of an object or using a respective; single detector pixel while at least a part of the interferometer is moved past said single detector pixel in the scan operation;

applying, for a given image pixel position as per said geometrical ray, a beam hardening processing operation with respect to said intensity values, thereby obtaining at least one interferometric reference parameter including at least one of a reference intensity and a reference visibility for said image pixel position;

reconstructing from said intensity values and said at least one interferometric reference parameter at least one of a phase signal and a dark-field signal; and outputting at least one of said phase signal and said dark-field signal.

10. A method of producing calibration data for beam hardening effect processing in scanning phase contrast or dark-field imaging, comprising:

acquiring calibration detector readings in a blank scan and at least one phantom scan for a given thickness of a phantom body or a plurality of phantom scans for a variable thickness of the phantom body using a detector or an x-ray source of a scanning radiography imager;

reconstructing, per detector pixel and per thickness of the phantom body or blank scan, interferometric reference parameters from the calibration detector readings; and reconstructing, per image pixel and per the given thickness or the blank scan, a respective indicator parameter indicative of different mean attenuation levels as per the variable thickness of the phantom body or the blank scan.

11. The method according to claim 10, further comprising storing the interferometric reference parameters in association with respective ones of the indicator parameters according to the given thickness of the phantom body or the blank scan.

12. A non-transitory computer-readable medium having one or more executable instructions stored thereon, which, when executed by a processor, cause the processor to perform a method for processing data supplied by a scanning radiography imager having an x-ray source for emitting radiation, a detector for detecting radiation, and an interferometer arranged at least partly between the x-ray source and the detector, the method comprising:

receiving data as intensity values that correspond to one and a same geometrical ray, the intensity values being acquired using different detector pixels of the detector in a scan operation by the imager of an object or using a respective single detector pixel while at least a part of the interferometer is moved past the single detector pixel in the scan operation;

applying, for a given image pixel position as per the geometrical ray, a beam hardening processing operation with respect to the intensity values, thereby obtaining at least one interferometric reference parameter including at least one of a reference intensity and a reference visibility for the image pixel position;

reconstructing from the intensity values and the at least one interferometric reference parameter at least one of a phase signal and a dark-field signal; and outputting at least one of the phase signal and the dark-field signal.

* * * * *